(12) United States Patent
Pierson et al.

(10) Patent No.: US 8,016,161 B2
(45) Date of Patent: Sep. 13, 2011

(54) PACKAGE AND DISPENSING SYSTEM

(75) Inventors: Paul Richard Pierson, Camden, DE (US); Curt E. Metzbower, Washington Crossing, PA (US); Robert J. Pieroni, Milford, DE (US)

(73) Assignee: Dentsply International, Inc., York, PA (US)

( * ) Notice: Subject to any disclaimer, the term of this patent is extended or adjusted under 35 U.S.C. 154(b) by 602 days.

(21) Appl. No.: 11/451,108

(22) Filed: Jun. 12, 2006

(65) Prior Publication Data

US 2008/0041879 A1    Feb. 21, 2008

(51) Int. Cl.
*B67D 7/70* (2010.01)

(52) U.S. Cl. .......... 222/137; 222/145.6; 222/541.6; 222/541.9

(58) Field of Classification Search .......... 222/137, 222/541.6, 541.9, 326, 327, 94, 129; 215/46, 215/47, 48, 49
See application file for complete search history.

(56) References Cited

U.S. PATENT DOCUMENTS

| | | | |
|---|---|---|---|
| 3,828,980 A * | 8/1974 | Creighton et al. | 222/137 |
| 4,624,667 A * | 11/1986 | Rutnarak | 604/414 |
| 4,708,650 A | 11/1987 | Holewinski et al. | |
| 5,271,527 A | 12/1993 | Haber et al. | |
| 5,725,499 A | 3/1998 | Silverstein et al. | |
| 5,743,436 A | 4/1998 | Wilcox et al. | |
| 6,247,617 B1 * | 6/2001 | Clyde et al. | 222/94 |
| 6,484,904 B1 * | 11/2002 | Horner et al. | 222/137 |
| 6,547,101 B1 | 4/2003 | Sogaro | |
| 6,843,652 B2 | 1/2005 | Xie et al. | |
| 6,874,665 B2 * | 4/2005 | Doherty et al. | 222/541.5 |
| 7,306,130 B2 * | 12/2007 | Brugner | 222/541.6 |
| 2002/0175185 A1 * | 11/2002 | Pierson | 222/145.5 |

FOREIGN PATENT DOCUMENTS

| | | |
|---|---|---|
| WO | WO 91/05931 | 5/1991 |
| WO | WO 02/094683 | 11/2002 |
| WO | WO 2006/060628 | 6/2006 |

* cited by examiner

*Primary Examiner* — Kevin P Shaver
*Assistant Examiner* — Daniel R Shearer
(74) *Attorney, Agent, or Firm* — Douglas J. Hura; David A. Zdurne; Leana Levia

(57) ABSTRACT

A package (10) for the storage and dispensing of a plurality of materials includes a first and a second longitudinally juxtaposed barrels (11, 12). Each barrel (11, 12) having a first and a second end (20, 21). Each first and second barrels (11, 12) having a quantity of at least one of the materials initially contained therein, and each barrel having an open end (20) and a dispensing end (21). A sealing plunger (40) disposed in each barrel (11, 12) such that the material in each barrel (11, 12) is initially positioned between the dispensing end (21) of the barrels (11, 12) and the respective ones of the sealing plungers (40). A snap cap (23) is contiguously formed to initially close each of the dispensing ends (21) of the barrels (11, 12), such that the snap cap (23) may be broken from the barrels (11, 12) to thereby forming a secondary open end (22) at the dispensing end (21) of the barrels (11, 12), thereby facilitating the material contained in each barrel (11, 12) to flow through and be dispensed.

4 Claims, 18 Drawing Sheets

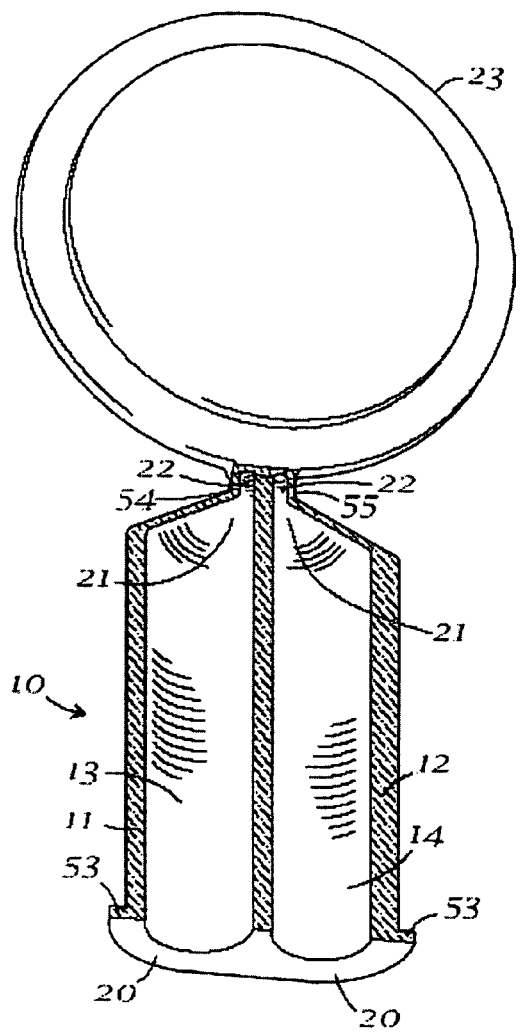
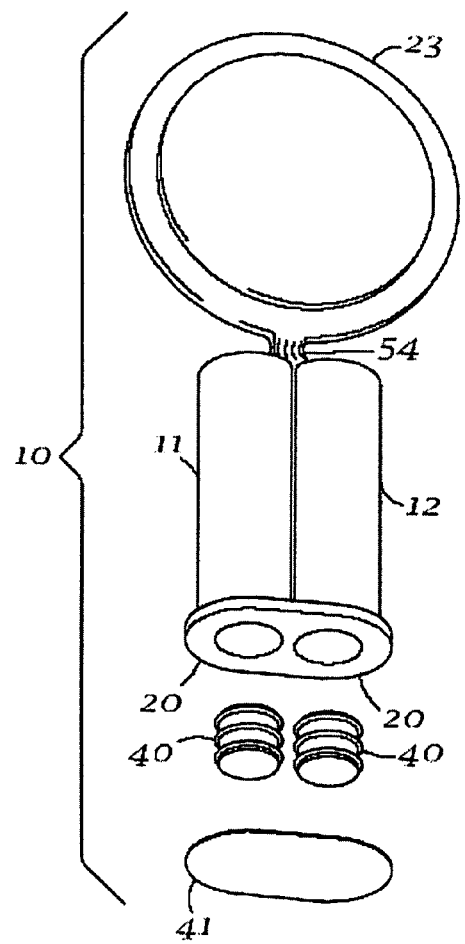
Fig. 1
Fig. 2

Fig. 8
Fig. 9
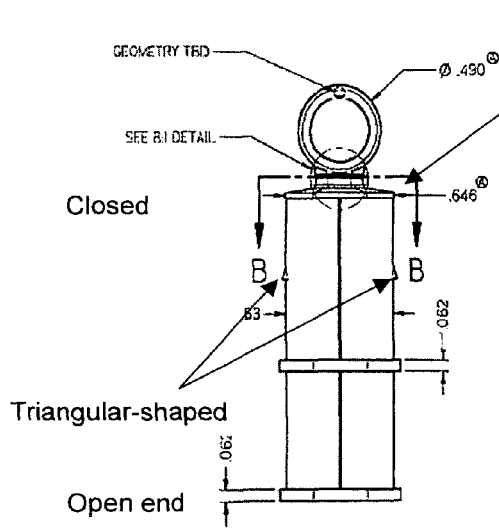
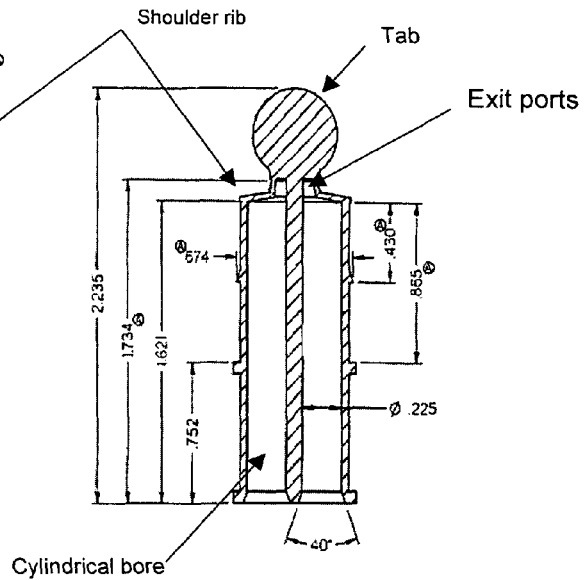

Tab
V-groove
Sealing bead
Cartridge body
Cartridge neck

Exit ports
Shoulder rib
Fracture plane
Neck
Bottom half of V-groove

Fig. 12
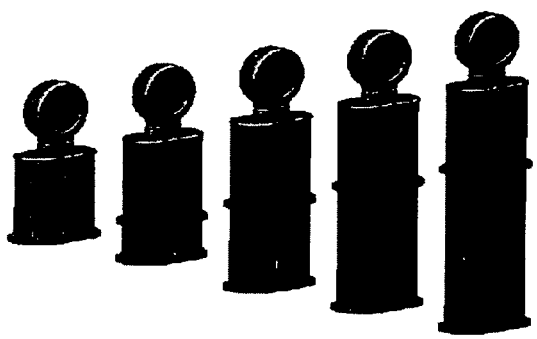
DC UNIT-DOSE FAMILY OF CARTRIDGES
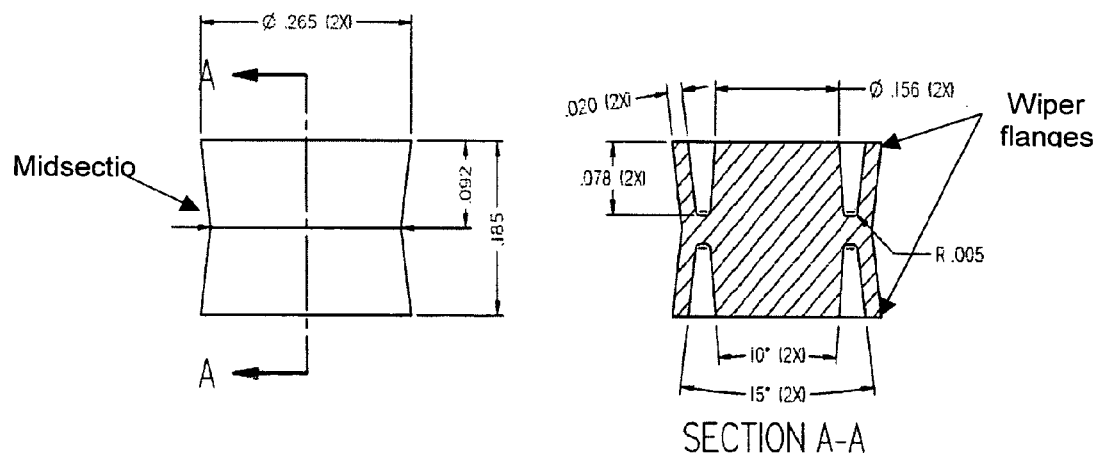
Fig. 13                     Fig. 14

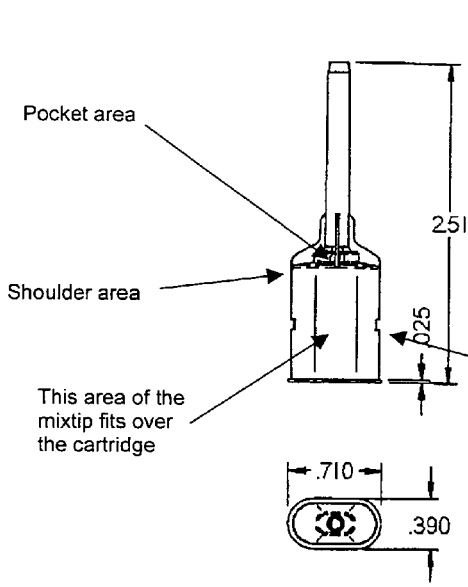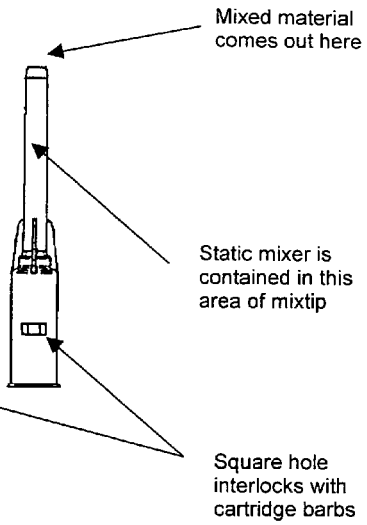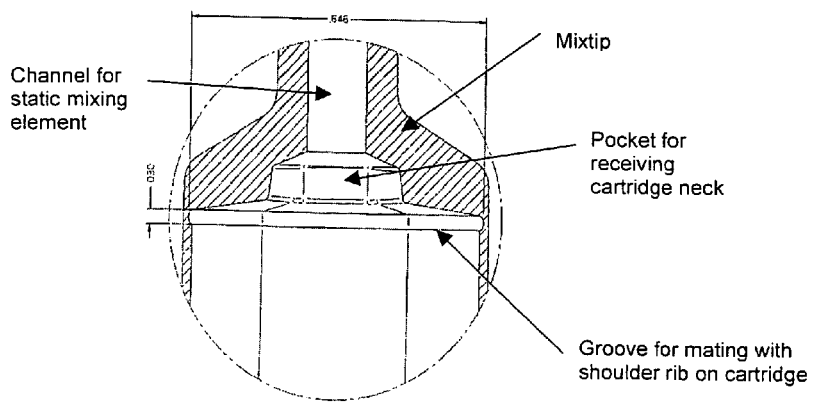

Detailed cross section view of cartridge neck in mixtip pocket

Fig. 23
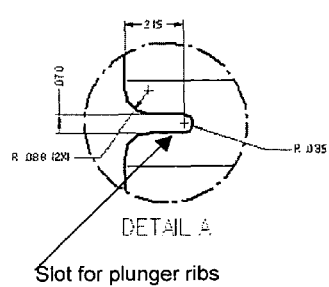
Slot for plunger ribs
Fig. 24
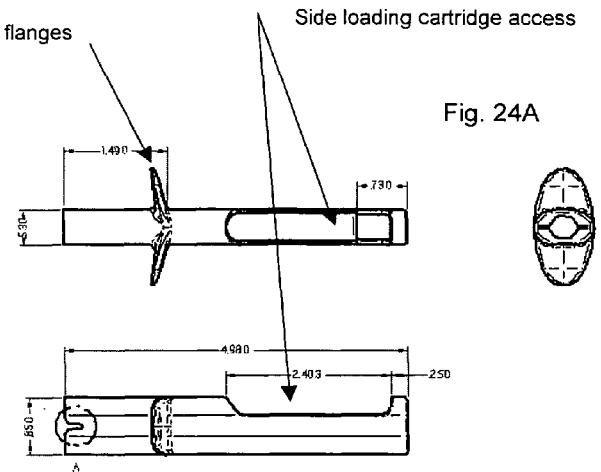
Finger flanges
Side loading cartridge access
Fig. 24A
Fig. 25
Fig. 26
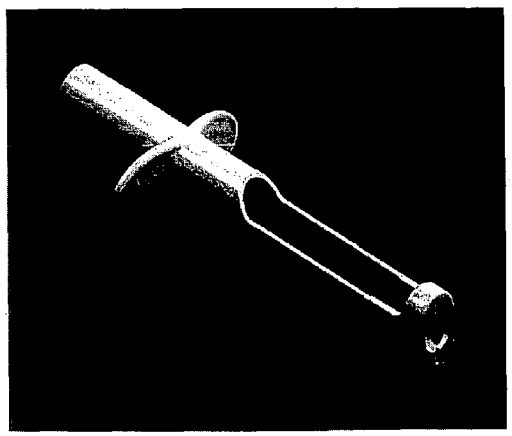
Fig. 27
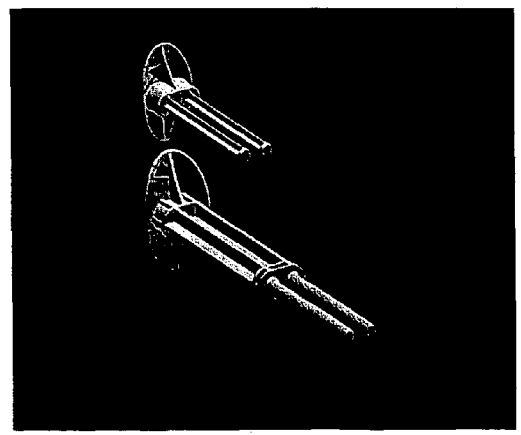

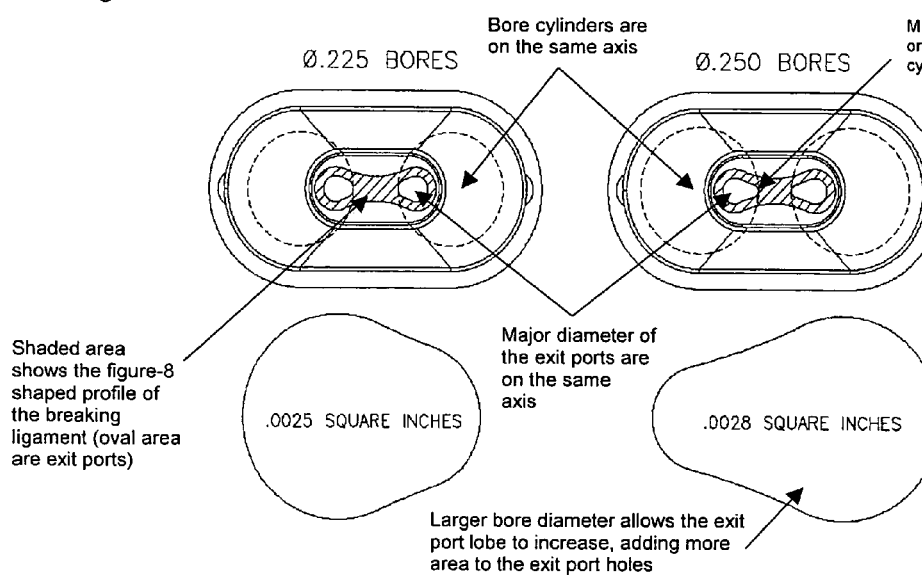

Circular ribs on outside of small cylinder permit cartridge to fit universal mixtip Small bore    Large bore

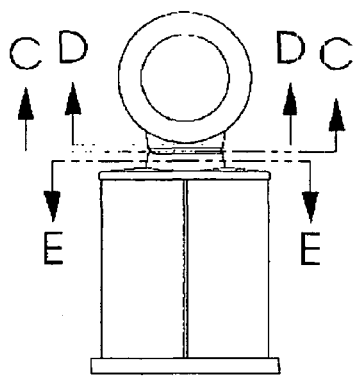
Fig. 41
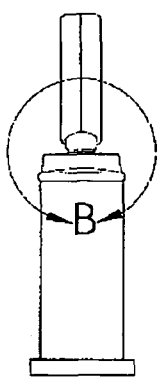
Fig. 43
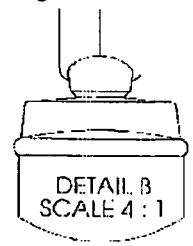
Fig. 44
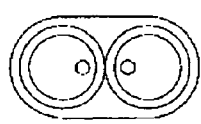
Fig. 42
 SECTION D-D Fig. 45
 SECTION C-C BREAKING PLANE Fig. 46
 SECTION E-E Fig. 47
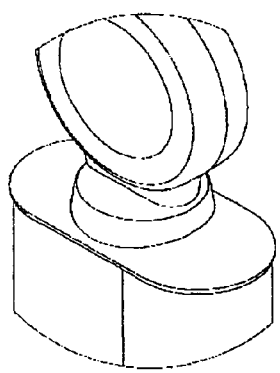
Fig. 48

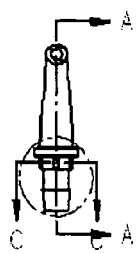
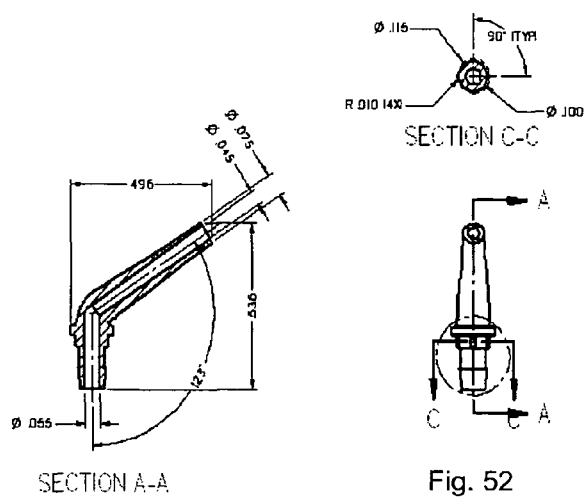
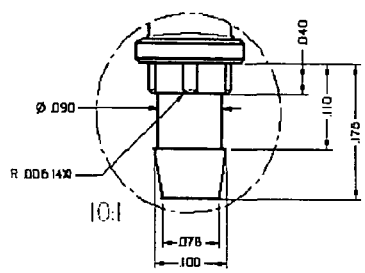
Fig. 51
Fig. 49
Fig. 50
Fig. 52
Fig. 53
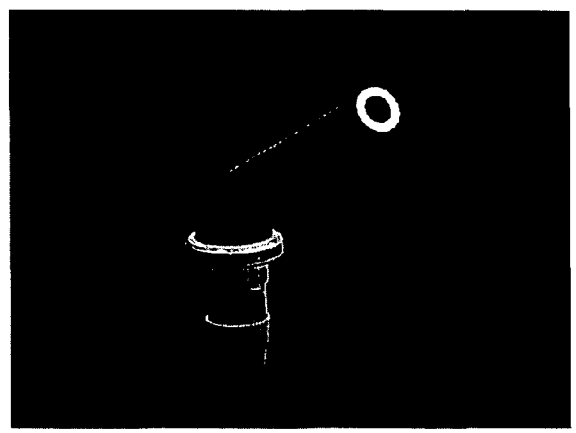
Fig. 54

PACKAGE AND DISPENSING SYSTEM

RELATED APPLICATIONS

This application claims the benefit of U.S. Provisional Application Ser. No. 60/633,085 filed on Dec. 3, 2004; and also claims the benefit of U.S. Provisional Application Ser. No. 60/657,749 filed on Mar. 2, 2005 (LDC-967A).

TECHNICAL FIELD

The invention is directed to a package and dispensing system for flowable, liquid, gel or paste materials, such as dental materials or the like, and has particular application to multi-component materials that are stored separately and mixed before use. The invention has application outside the dental industry (such as for example, with commercial epoxies, industrial adhesives and medical cements) but will be exemplified herein with respect to dental products for illustrative purposes only. More particularly, the invention relates to a multiple-barrel storage and dispensing cartridge having a snap-open cap. The invention also relates to a unit dose, cartridge delivery system. The cartridges may include a plurality of unit dose sizes and may be used in conjunction with a universal mixtip and handpiece system. The components may be disposable.

BACKGROUND OF THE INVENTION

Certain materials require specialized packaging for storage and dispensing of the material. For example, with respect to fluid or fluid-like (that is, having an ability to flow either due to gravity or to an applied force) dental materials, the materials may be light sensitive or the like, requiring packaging the prevents premature exposure of the material to light. Further, dental materials such as adhesives, often contain multiple components that need to be separated during storage but that must be mixed immediately prior to use. Further still, it is often necessary to use only a small amount of a material for a given dental procedure. Hence, it is desirable to store and dispense such materials in single use or "unit dose" sizes.

Heretofore, storage and packaging of dental materials was often accomplished with small opaque bottles. While such bottles often provided for ease of storage, they do not lend themselves well to efficient dispensing operations. Further, when two or more components are to be mixed, the materials have to first be accurately measured.

Historically, paste/paste products have been packaged in double-barrel syringes with motionless mixing tips. MixPac, TAH industries and Plas-Pak are several companies that manufacture and market double-barrel syringes and mixtips. Double barrel syringes are available in standard 2.5 and 5 mL formats. These syringes are suitable for unit-dose applications where the unit of use is approximately 2.5 and 5 mL, but when the unit of use is less than 2.5 mL they are only suitable for multi-use applications. Therefore, there is a need for a unit-dose, auto-mixing system for paste/paste products where the unit of use is equal to or less than 2.5 mL.

For example, when cementing a crown onto a tooth, approximately 0.3 mL of cement is needed. It would be wasteful to package a unit-dose amount in a double barrel syringe that was designed for 2.5 mL. As a result, the only viable auto-mix packaging solution for paste/paste cements is a multi-use double barrel syringe.

The present invention seeks to create a true unit-dose packaging and delivery system for the range of paste/paste products that are used in volumes of 2.5 mL or less. In order to achieve the small volumes needed for some dental products a small cartridge was conceived (sometimes referred to as the base unit cartridge, see also FIG. 15). A cartridge that delivers a net 0.3 mL is practical with regards to this design. Adding incremental extensions onto the length of the base cartridge can make cartridges of larger net volumes.

Another example is when a dental practitioner takes an impression by the dual-phase technique. Users commonly back-fill an intra-oral syringe with low viscosity mixed impression material using a standard 50 mL cartridge and mixtip. GC America manufactures an intermediate intra-oral syringe for the dual-phase technique. The intra-oral syringe improves the technique of applying low viscosity impression material to the prepared tooth. Once the mixed product is in the syringe, it must be used immediately or else it would set up due to the reaction of mixing the two components. The syringe is usually loaded with more than enough material to perform the procedure and must be cleaned and sterilized after use. This procedure provides good clinical technique, but it is cumbersome and wastes a lot of product.

The present unit-dose cartridge delivery system offers the practitioner the same syringe technique while improving ease of use. The system can be assembled and staged prior to use thereby reducing the complexity of the technique and eliminating the critical timing needed to use a back-filled syringe. The technique of using a back-filled syringe wastes about 3 mL of product in order to deliver the 1 mL needed for the procedure (approximately 2 mL in the mixtip and 1 mL in the intra-oral syringe). The system wastes only about 0.3 mL of product because the mixtip is much smaller than that of the standard 50 mL cartridge system and an intermediate delivery syringe is not needed.

It should therefore be understood that the present cartridge delivery system reduces wasted product and packaging, improves ease of use and provides true unit-dose, auto-mixing packaging options for products that are used in amounts of 2.5 mL and less.

A need exists therefore, for a package for storing a material and for dispensing the material, especially a dental material such as a multi-component adhesive. The package should protect the material to premature exposure to the environment; it should keep multiple components separate during storage; it should facilitate the dispensing and mixing of premeasured quantities of the material; and, it should be useful for unit dose quantities of the material to be packaged. A need also exists for an improved delivery and dispensing system for use with such a package.

DISCLOSURE OF THE INVENTION

It is therefore, and object of the present invention to provide a package for fluid or fluid-like (herein collectively referred to as "fluid") materials.

It is another object of the invention to provide a package as above, with the ability to store a plurality of components.

It is another object of the invention that the package, as above, prevents exposure of the contained material or materials to the environment until desired.

It is a further object of the invention to provide a package as above, useful in unit dose quantities of the packaged materials.

It is yet another object of the invention to provide a package that is easily and efficiently useful to an operator.

These and other objects of the invention, which will become apparent from the invention as described herein, are accomplished by the invention as hereinafter described and claimed.

In general, a package for the storage and dispensing of a plurality of materials comprises a first and a second longitudinally juxtaposed barrels; each said barrel having a first and a second end; each said first and second barrels having a quantity of at least one of the materials initially contained therein; each said barrel having an open end and a dispensing end; a sealing plunger disposed in each said barrel such that the material in each said barrel is initially positioned between said dispensing end of said barrels and the respective ones of said sealing plungers; a snap cap contiguously formed to initially close each of said dispensing ends of said barrels; such that said snap cap may be broken from said barrels to thereby forming a secondary open end at said dispensing end of said barrels, thereby facilitating the material contained in each said barrel to flow through and be dispensed.

A storing and dispensing system a plurality of materials also comprise a first and a second longitudinally juxtaposed barrels; each said barrel having a first and a second end; each said first and second barrels having a quantity of at least one of the materials initially contained therein; each said barrel having a primary open end and a dispensing end; a sealing plunger disposed in each said barrel such that the material in each said barrel is initially positioned between said dispensing end of said barrels and the respective ones of said sealing plungers; a snap cap contiguously formed to initially close each of said dispensing ends of said barrels; such that said snap cap may be broken from said barrels to thereby forming a secondary open end at said dispensing end of said barrels, thereby facilitating the material contained in each said barrel to flow through and be dispensed; and, a dispensing gun having a first and a seconded laterally displaceable gun plungers, and an actuating means for laterally displacing said gun plungers; said first and second barrels having means to removably affix said barrels to said gun; said first gun plunger being receivable within said primary open end of said first barrel, and being laterally displaceable therethrough to contact said seal plunger located in said first barrel; and, said second gun plunger being receivable within said primary open end of said second barrel, and being laterally displaceable therethrough to contact said seal plunger located in said second barrel.

A package for the storage and dispensing of a plurality of materials also comprises a first and a second longitudinally juxtaposed barrels; each said barrel having a first and a second end; each said first and second barrels having a quantity of at least one of the materials initially contained therein; each said barrel having an open end and a dispensing end; a sealing plunger disposed in each said barrel such that the material in each said barrel is initially positioned between said dispensing end of said barrels and the respective ones of said sealing plungers; a snap cap contiguously formed to initially close each of said dispensing ends of said barrels; such that said snap cap may be broken from said barrels to thereby forming a secondary open end at said dispensing end of said barrels, thereby facilitating the material contained in each said barrel to flow through and be dispensed; and a mix-tip removably affixed to said first and second barrels and having a dispensing aperture, such that the material that is dispensed from said secondary openings is caused to flow through said mixtip, and out through said dispensing aperture; a static mixing element contained within said mixtip to promote intimate contact and mixing of the materials.

A storing and dispensing system a plurality of materials also comprises a first and a second longitudinally juxtaposed barrels; each said barrel having a first and a second end; each said first and second barrels having a quantity of at least one of the materials initially contained therein; each said barrel having a primary open end and a dispensing end; a sealing plunger disposed in each said barrel such that the material in each said barrel is initially positioned between said dispensing end of said barrels and the respective ones of said sealing plungers; a snap cap contiguously formed to initially close each of said dispensing ends of said barrels; such that said snap cap may be broken from said barrels to thereby forming a secondary open end at said dispensing end of said barrels, thereby facilitating the material contained in each said barrel to flow through and be dispensed; and, a dispensing gun having a first and a seconded laterally displaceable gun plungers, and an actuating means for laterally displacing said gun plungers; said first and second barrels having means to removably affix said barrels to said gun; said first gun plunger being receivable within said primary open end of said first barrel, and being laterally displaceable therethrough to contact said seal plunger located in said first barrel; and, said second gun plunger being receivable within said primary open end of said second barrel, and being laterally displaceable therethrough to contact said seal plunger located in said second barrel; and a foil seal initially closing said primary open ends of said first and second barrels, such that when said gun plungers are caused to be laterally displaced into and received by said barrels, said foil seal is first caused to be punctured by physical contact with said gun plungers.

The invention also provides a packaging and delivery system for fluid, gel or paste-like products that are made up of two separate and distinct compositions that must be mixed together prior to application. In particular, the invention is advantageous for the unit-dose application of dental materials. Current dental applications include, but are not limited to impression materials, bite registration materials, tissue management materials, endodontic materials, rubber dams, resin based core build-up materials, resin based temporary material, resin based permanent and temporary cements, adhesives, calcium hydroxide pulp-capping materials and tooth bleaching products. It should also be recognized that there might be other product applications outside of the dental industry that would similarly benefit from this invention such as commercial epoxies, industrial adhesives or medical cements, just to name a few.

BRIEF DESCRIPTION OF THE DRAWINGS

FIG. 1 is a sectional, top plan view of a package according to the invention.

FIG. 2 is a perspective view of a package according to the invention, showing component parts in an exploded manner.

FIG. 8 is a front elevational view of an alternative embodiment of the invention.

FIG. 9 is a side, sectional view of the embodiment of FIG. 8.

FIG. 12 shows a progressive series of devices as in FIG. 8 configured to hold and dispense different amounts of material.

FIG. 13 shows a front elevational view of an alternative embodiment of the invention.

FIG. 14 is a front, sectional view of the embodiment of FIG. 13.

FIG. 15 shows a mixing tip useful with the present invention.

FIG. 16 shows an end view of the tip of FIG. 15.

FIG. 17 shows a side view of the tip of FIG. 15.

FIG. 18 is a close up view of one portion of the embodiment of FIG. 15.

FIG. 23 is a close up view of one portion of a plunger useful in the practice of the present invention.

FIG. 24 is a top view of a plunger useful in the practice of the present invention.

FIG. 25 is a side view of the plunger of FIG. 24.

FIG. 24A is an end view of the plunger of FIG. 24.

FIG. 26 is a perspective view of the plunger of FIG. 24.

FIG. 27 shows a series of alternative plunger assemblies.

FIG. 32 shows a top plan view of a device as in FIG. 31.

FIG. 33 shows a top plan view of a device as in FIG. 31.

FIG. 34 shows a schematic view of a bore shape of one of the devices of FIG. 31.

FIG. 35 shows a schematic view of a bore shape of one of the devices of FIG. 31.

FIG. 41 shows a front, elevational view of an alternative device according to the present invention.

FIG. 42 shows a bottom view of the device as in FIG. 41.

FIG. 43 shows a bottom view of the device as in FIG. 41.

FIG. 44 shows a detail view of one portion B of the device of FIG. 41.

FIG. 45 shows a sectional view taken along lines D-D of FIG. 41.

FIG. 46 shows a sectional view taken along lines C-C of FIG. 41.

FIG. 47 shows a sectional view taken along lines E-E of FIG. 41.

FIG. 48 shows a close up, perspective view of one portion of the device of FIG. 41.

FIG. 49 shows a dispensing nozzle useful in the practice of the present invention.

FIG. 50 shows a side, sectional view of the device of FIG. 49, taken along lines A-A of FIG. 52.

FIG. 51 shows a top sectional view taken along lines C-C of FIG. 52.

FIG. 53 shows a close up view of one portion of the device of FIG. 52.

FIG. 54 shows another perspective view of the device of FIG. 49.

PREFERRED EMBODIMENTS FOR CARRYING OUT THE INVENTION

Figure 3:
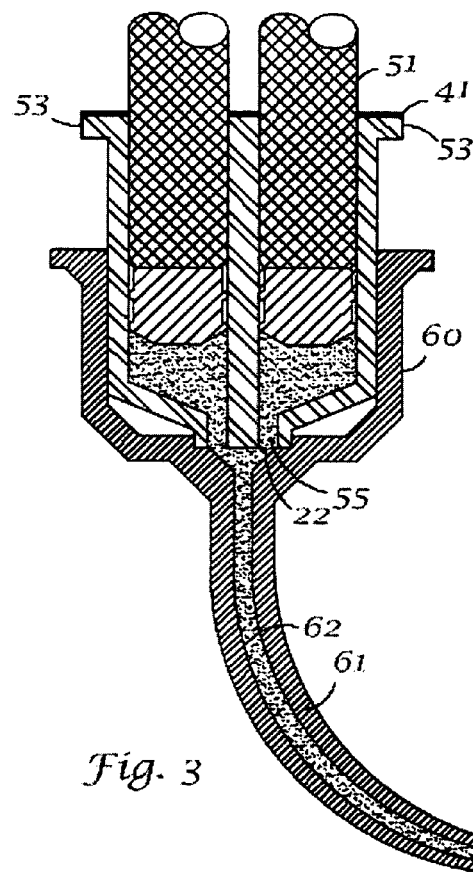
FIG. 3 is a front elevational view of a package according to the present invention, showing part of an optional plunger and an optional mix tip in place upon the package.
Figure 4:
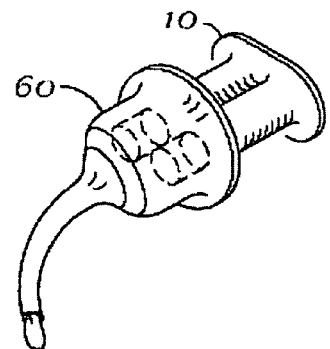
FIG. 4 is a perspective view of a package according to the invention, also showing an optional mix-tip.
Figure 5:
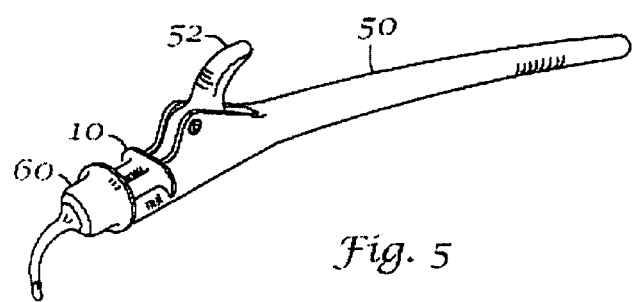
FIG. 5 is a perspective view as in FIG. 4, showing the inventive device affixed to a dispensing gun.

A multiple component, unit-dose container delivery system according to the invention is shown by way of example on the drawings by the number 10. Package 10 can be used for the storing and dispensing of any type or quantity of material, but is particularly suited for storing and dispensing of dual-component dental adhesives or the like.

Package 10 includes a plurality of barrels, such as barrels 11 and 12. Package 10 is exemplifies with two barrels 11 and 12, it being understood that any numbers of such barrels is within the scope of the invention. Barrels 11 and 12 are preferably elongate having open areas 13 and 14 respectively therein.

Barrels 11 and 12 are preferably juxtaposed in their longitudinal direction, although other configurations are within the scope of the invention. Further, each barrel 11 and 12 is provided with a first, primary opening end 20 and a second end 21, each of the first ends 20 being provided with a primary opening allowing access to open areas 13 and 14 respectively.

Figure 6:
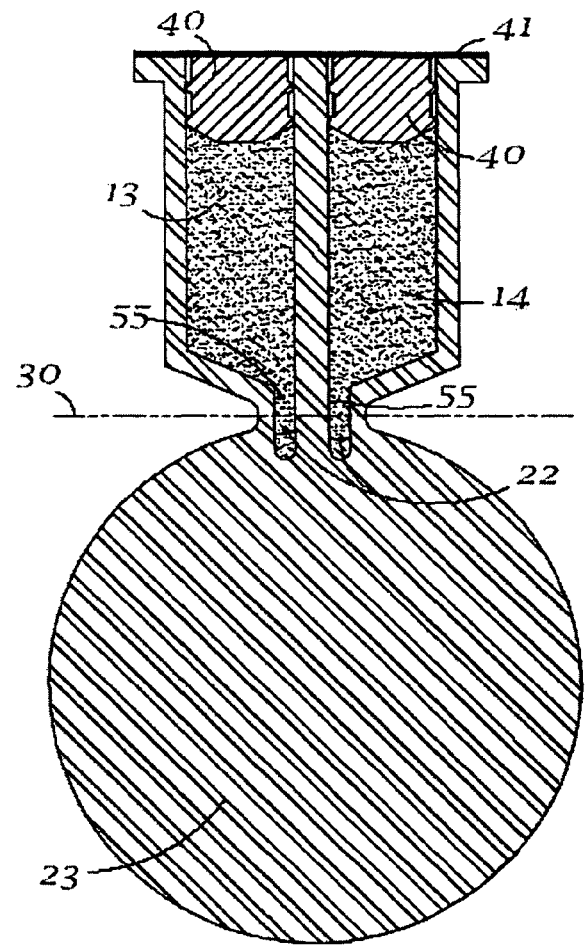
FIG. 6 is a front elevational, sectional view of a package according to the present invention.
Figure 7:
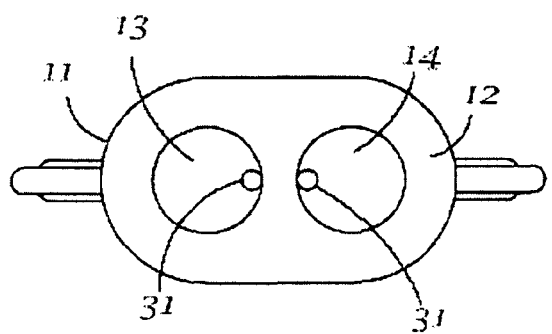
FIG. 7 is a top, plan view of one end of the inventive package with its snap-cap removed.

Each of the second ends 21 of barrels 11 and 12 is provided with a dispensing aperture 22 that is initially closed by snap-cap or break-cap 23. Preferably, snap-cap 23 is integrally formed with barrels 1 and 12. Further, snap-cap 23 can be broken from barrels 11 and 12 by snapping or breaking it therefrom, such as at break point 30 (FIG. 6) or some other location. Preferably when snap-cap 23 is broken from barrels 11 and 12, secondary openings 31 are formed in each of said barrels 11 and 12, such that open areas 13 and 14 can fluidly communicate therethrough, allowing for the dispensing of the materials through secondary openings 31. Preferably, barrels 11, 12 and snap cap 23 are formed from a suitable plastic material that will allow the breaking operation. More preferably, such components are preferably formed as a single unit in for example, an injection molding operation or the like.

There is also provided, a plurality of seal plungers 40, preferably at least equal to the number of barrels 11 and 12 employed. The material (not shown) to be dispensed is initially placed into open areas 13 and 14 by input through primary open ends 21 in each said barrel 13, 14. Seal plungers 40 are receivable within open areas 13 and 14, through primary openings 20, such that the material is between said seal plungers 40 and said snap-cap 23, effecting the storage function of the package 10. In this configuration, the materials within barrels 11 and 12 are prevented from being exposed to the environment. When it is desired to dispense the material, snap-cap 23 is broken from package 10, thereby creating secondary opening 22 that fluidly communicate between open areas 13 and 14 and the environment. Seal plungers are preferably formed from a deformable plastic, rubber, rubber-like or elastomeric material and dimensioned to fit snugly within open areas 13, 14, to effectively seal the open areas 13, 14 from the environment through primary openings 20.

After seal plungers 40 are received through primary openings 20 and into open areas 13 and 14, openings 20 may be further sealed with any type of layer, such as foil layer 41.

To further facilitate the dispensing of the material through secondary openings 22, a dispensing gun 50 of any design may be employed. One preferred dispensing gun has at least one gun plunger 51, and preferably the same number of gun plungers as barrels 11, 12 are present in package 10, although this is not necessary. Further still, gun 50 should have some means such as hand-lever 52 to laterally displace gun plungers toward primary openings 20 when package 10 is mounted upon gun 50. Further, package 10 should be provided with some means to removably secure package 10 to gun 50, such as lips or shoulders 53 that interact such as by a friction or snap fit to gun 10, to thereby removably secure package 10 thereto. An exemplary such gun is found in for example, commonly assigned U.S. Pat. No. 4,708,650, which is hereby incorporated by reference for such disclosure. When gun plungers 51 are laterally moved toward barrels 11, 12, the foil layer 41 may be physically impinged by and then punctured by gun plungers 51, or the foil layer 41 may be removed before such action. Further, as gun plungers 51 are laterally displaced toward barrels 11, 12, they will be received through primary openings 20 and into open areas 13, 14, to thereby physically contact plunger seals 40. Continued lateral displacement of gun plungers 51 toward end 21 of barrels 11, 12 will cause the material between end 21 and plunger seals 40 to be forced or moved toward second ends 21, to be dispensed through secondary openings 22.

A neck area 54 may be provided between snap-cap 23 and second ends 21 of barrels 11, 12, preferably such that passages 55 extend from open areas 13, 14 and at least partially into neck area 54. By being of a reduced size as compared to snap-cap 23 and/or barrels 11,12, the break area 30 is facilitated by neck area 54. Break area 30 is preferably located such that passages 55 extend on either side thereof, such that when snap-cap 23 is broken from barrels 11, 12, secondary openings 22 are thereby formed to fluidly communicate with the exterior of package 10.

Package 10 may also be provided with an integral or preferably removable mix-tip 60, such that the material dispensed through secondary openings 22 is first mixed within a mix-tip dispensing tube 61. Tube 61 may even be provided with a static mix element 62, which may be a twisted wire or the like. The material from barrels 11 and 12 are combined and mixed within tube 61, preferably the mixing being enhanced by mix element 61. Tube 61 is provided with dispensing opening 63, fluidly communicating between the interior of tube 61 and the environment. Brush bristles 64 may be located adjacent, within or surrounding dispensing opening 63 of mix tip 60, to facilitate application of the dispensed materials.

Mix-tip 60 is preferably removably affixable to package 10. Any conventional means of affixing mix-tip 60 to package 10 is within the scope of the invention, such as adhesively bonding, or more preferably by a friction of snap fit. For example, detents 70 may be provided in the mix-tip 60 interior to match and receive nubs 71, thereby holding mix-tip 60 to package 10. Nubs 71 and/or detents 70 may be formed from a plastic or other deformable material, to facilitate placement of mix-tip 60 upon package 10. Of course, package 10 may carry detents 70 and mix-tip 60 could carry nubs 71 (not shown), and still fall within the scope of the invention.

The size dimensions of package 10 may vary depending upon the nature of the materials to be dispensed, but is preferably of a unit-dose size for such materials. Double, triple or multiple unit dose sizes are also within the scope of the invention.

Figure 10:
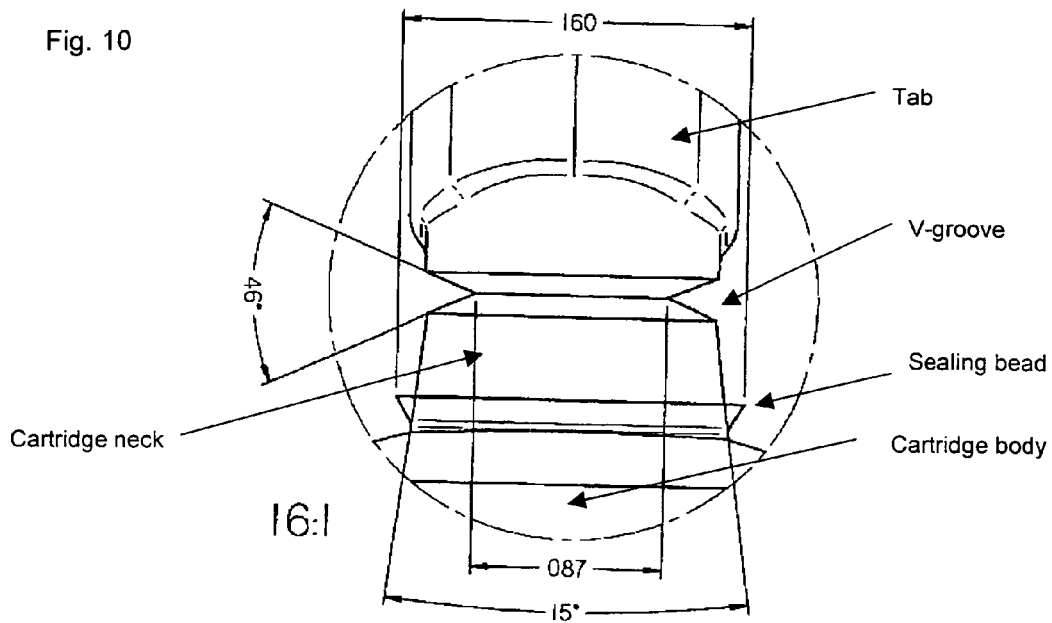
FIG. 10 is a close up view of one portion of the embodiment of FIG. 8.
Figure 11:
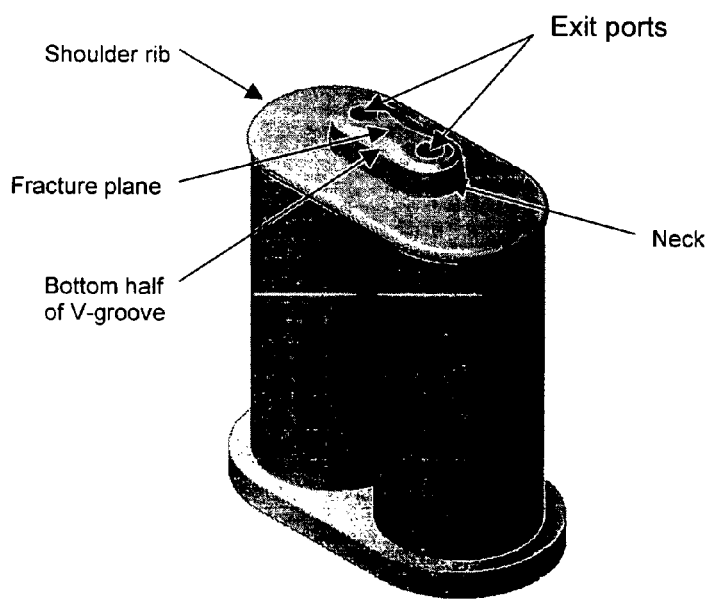
FIG. 11 is a perspective view of the barrel portion of FIG. 8.
Figure 19:
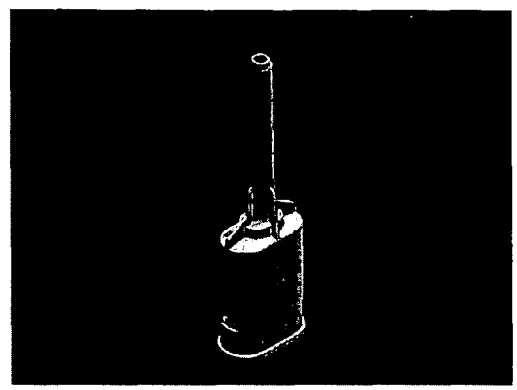
FIG. 19 is a perspective view of the tip of FIG. 15.
Figure 20:
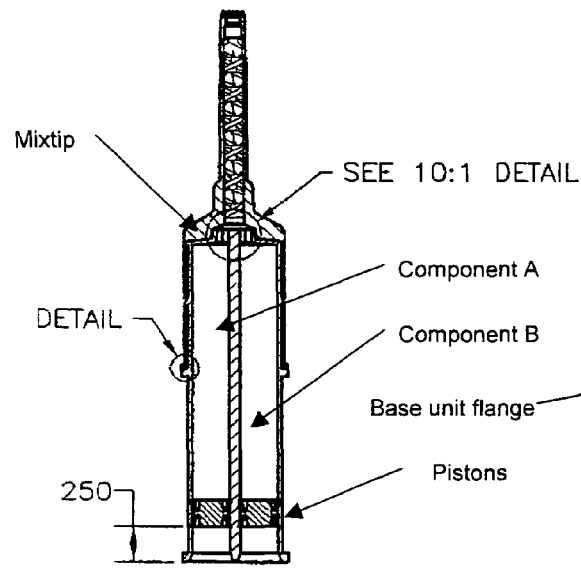
FIG. 20 is a front, sectional view of the embodiment of FIG. 15.

In another embodiment of the invention, a storage and dispensing system includes a cartridge (FIGS. 8 and 9) that has two parallel cylindrical bores. The cartridge is open at one end for filling and closed at the other end. The cartridge, including the closed end is formed as one contiguous piece of material. The cartridge is filled with product (for example, a two-component product consisting of a base and catalyst) from the open end and is sealed with pistons that fit frictionally in the cylindrical bores (FIG. 20). The closed end has a section of reduced thickness that is referred to as a breaking ligament, whereby the user can break open the cartridge. The breaking ligament is defined by a small V-groove that runs around the perimeter of the neck area and is shown in FIG. 8 at section line BB (also shown in FIG. 10). A tab at the closed end aids the user in applying enough leverage to snap the narrow breaking ligament. The V-groove acts to concentrate the stress across the neck in such away that the ligament fractures along the intended breaking plane. Removing the tab opens up two small exit ports that extend across the plane of the breaking ligament (FIG. 11).

Preferably, the cartridge is made from a brittle plastic (as opposed to a ductile plastic) that will snap open when the tab is broken off. Cyclic olefin copolymer (COC) and polypropylene (PP) homopolymer have both been used successfully as cartridge materials. The cartridge can be made from opaque plastic (for products that require light protection) or they can be made from translucent plastic in order to allow the user to visualize how much is left in the cartridge. In use, the cartridge material should provide appropriate barrier properties for the products contained within the cylinders. It should therefore be recognized that different products might require different cartridge materials and there may be many suitable materials of construction for the cartridge depending upon the desired end use and nature of the material contained within the package.

Figure 31:
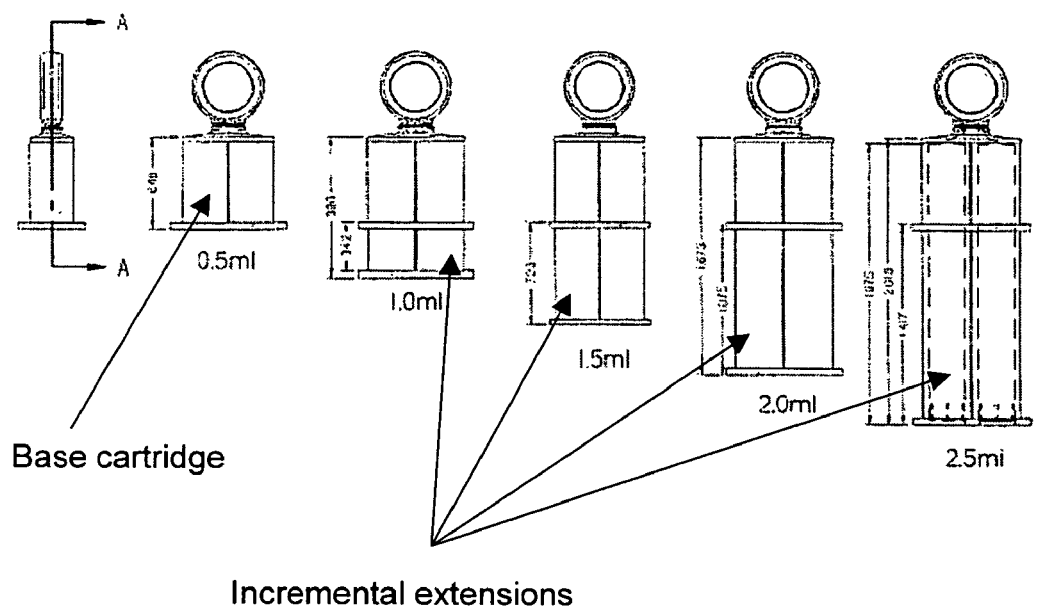
FIG. 31 shows a progressive series of devices as in FIG. 8 configured to hold and dispense different amounts of material.

FIG. 12 illustrates a family of cartridges with a base unit and incremental extensions (see also FIG. 31). This configuration provides a cartridge delivery system that can be tailored to specific product requirements depending on the amount of material needed. This configuration is particularly useful for a wide range of unit-dose applications under about 2.5 mL.

The cartridge is ready for use after it has been filled with product and sealed with pistons (FIG. 13). The pistons are preferably substantially cylindrical shaped plugs that fit frictionally in the end of the cartridge. In this configuration, the pistons are symmetrical so that they do not have to be oriented top to bottom before insertion. Each end has an outward tapering wiper flange that contacts the sidewall of the cartridge cylinder. The outermost diameter of the wiper flange is slightly greater than the inside diameter of the cartridge cylinder. The midsection of the piston is slightly smaller than the ID of the cartridge cylinder. This produces an efficient configuration for the piston to conform to the inside wall of the cartridge (as shown in FIG. 20). Pistons with other shapes may also been used such as spheres and barrels.

In use, the cartridge tab is removed (as in FIG. 11) and the mixtip (FIG. 15) is pushed onto the cartridge like a tight fitting sheath. The mixtip is preferably made from ductile plastic such as high-density polyethylene (HDPE) so that it can stretch over the cartridge shoulder rib and triangular barbs without permanent deformation. The mixtip fits snuggly over the exterior of the cartridge and is locked in place by a small rib that runs around the shoulder of the cartridge (FIG. 8). The shoulder rib mates with a similarly shaped groove on the interior of the mixtip (FIG. 18). In addition, the cartridge has small preferably triangular-shaped barbs on each side (FIG.

8) that mate with preferably square holes in the mixtip (FIG. 15). The angle of the barbs allows the mixtip to slide on, but prevents it from pulling off once it is in place. The shoulder rib and the locking barbs combine to provide an effective mechanism for keeping the mixtip on the cartridge during the process of extruding material. It should be recognized that these features could be employed together or independently as needed.

As shown in FIG. 20, a mixtip has been assembled with a cartridge body. The mixtip has a small flange that runs around the perimeter of the end that receives the cartridge and is sometimes referred to as a skirt. The mixtip skirt abuts the base unit flange. FIG. 20 also shows the position of the pistons inside the cylindrical cartridge bores. In the preferred configuration, the mixtip fits the entire family of cartridges universally.

Figure 21:
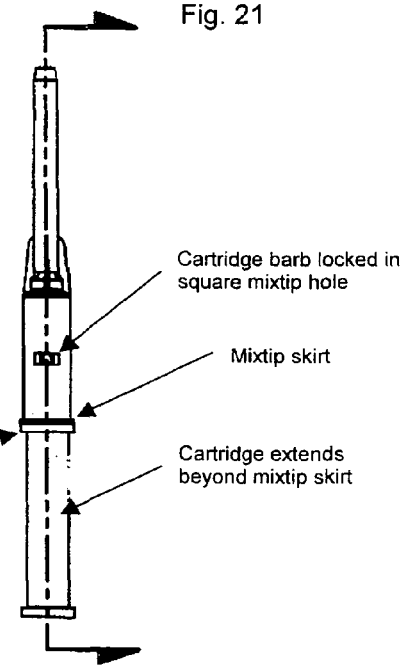
FIG. 21 is a side, sectional view of the embodiment of FIG. 15.
Figure 22:
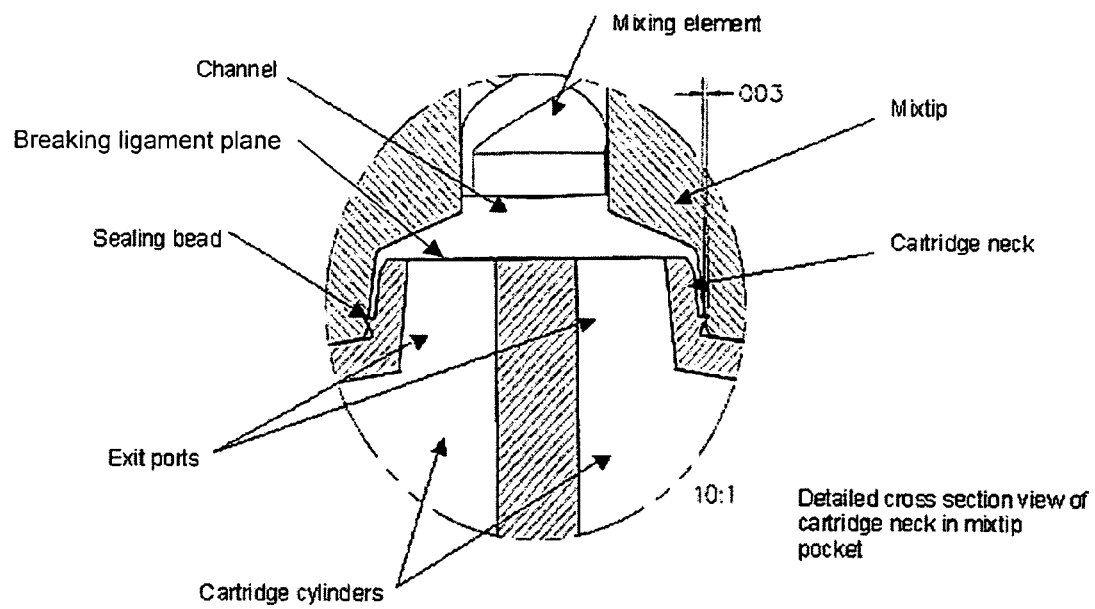
FIG. 22 is a close up view of one portion of the embodiment of FIG. 20.
Figure 28:
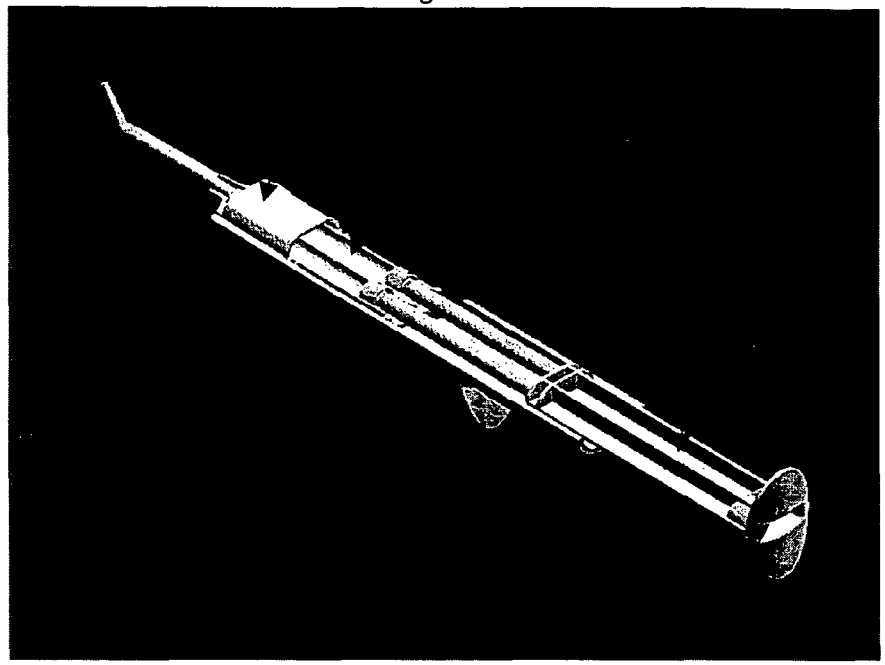
FIG. 28 is a perspective, partially cut away view of a plunger according to the invention.
Figure 29:
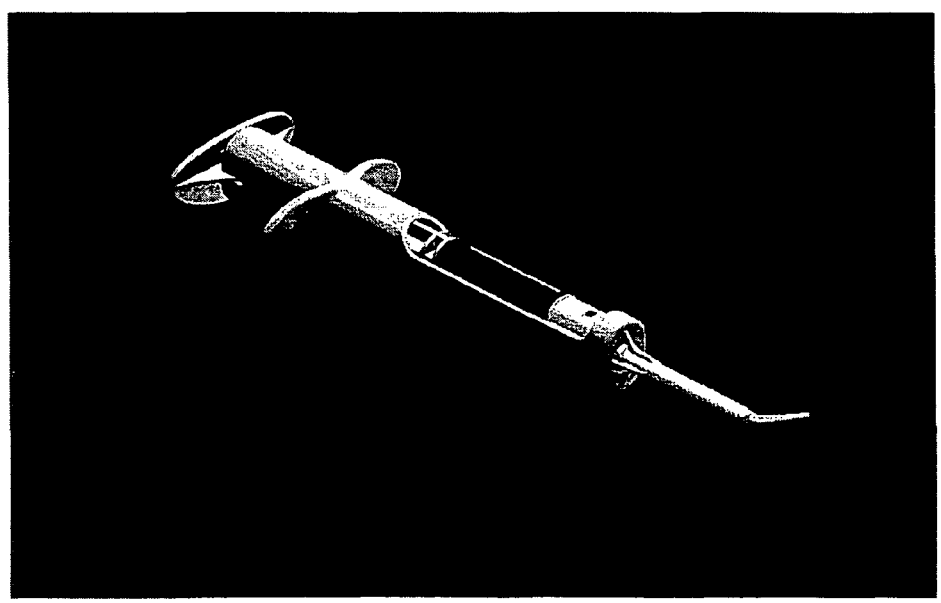
FIG. 29 is a perspective, partially cut away view of a plunger according to the invention.

The cartridge has a neck section below the plane of the breaking ligament (FIG. 22) that mates with a pocket in the mixtip. A small sealing bead runs around the perimeter of the cartridge neck and cuts into the soft plastic of the mixtip pocket, thereby forming a seal and preventing product from flowing backwards around the cartridge. The mixtip pocket terminates into a channel that houses the motionless mixing element. According to another aspect of the present invention, a handpiece is provided to hold the cartridge and dispense the material. In this configuration, the handpiece includes a reusable body and plunger (FIGS. 24-27). The cartridge and mixtip assembly (as shown in FIGS. 20 and 21) is placed in the handpiece though the side access opening in the body. Preferably, the side access opening is large enough to fit the largest cartridge thereby becoming a universal handpiece. An alternative end loading handpiece is also contemplated. The shoulder rib area of the cartridge assembly fits intimately in the handpiece. A snug fit at the shoulder rib holds the assembly together and prevents the mixtip from dislodging under the pressure of dispensing. The handpiece supports the assembly in front of the shoulder area so that it cannot be accidentally dislodged from excessive pressure (FIGS. 28 and 29 illustrate the assembled handpiece, mixtip and cartridge). The handpiece has two plunger rods that are on the same axis as the cartridge cylinders. The user pushes the plunger, causing the pistons to displace the material through the cartridge cylinders and out the exit ports. The material then flows over the motionless mixer and is efficiently mixed for use. It should be appreciated that a variety of different dispensers could be employed to provide the needed force and motion of the plungers.

The handpiece plunger may be provided with a pocket in the end that can be used for breaking off the cartridge tab (FIG. 28). The user holds the plunger in one hand and slips the cartridge tab into the pocket. The plunger is used to apply leverage to the tab making the task of breaking it off easier. The tab can also be broken off without using the pocket and just using finger pressure and a firm grip on the tab.

Figure 30:
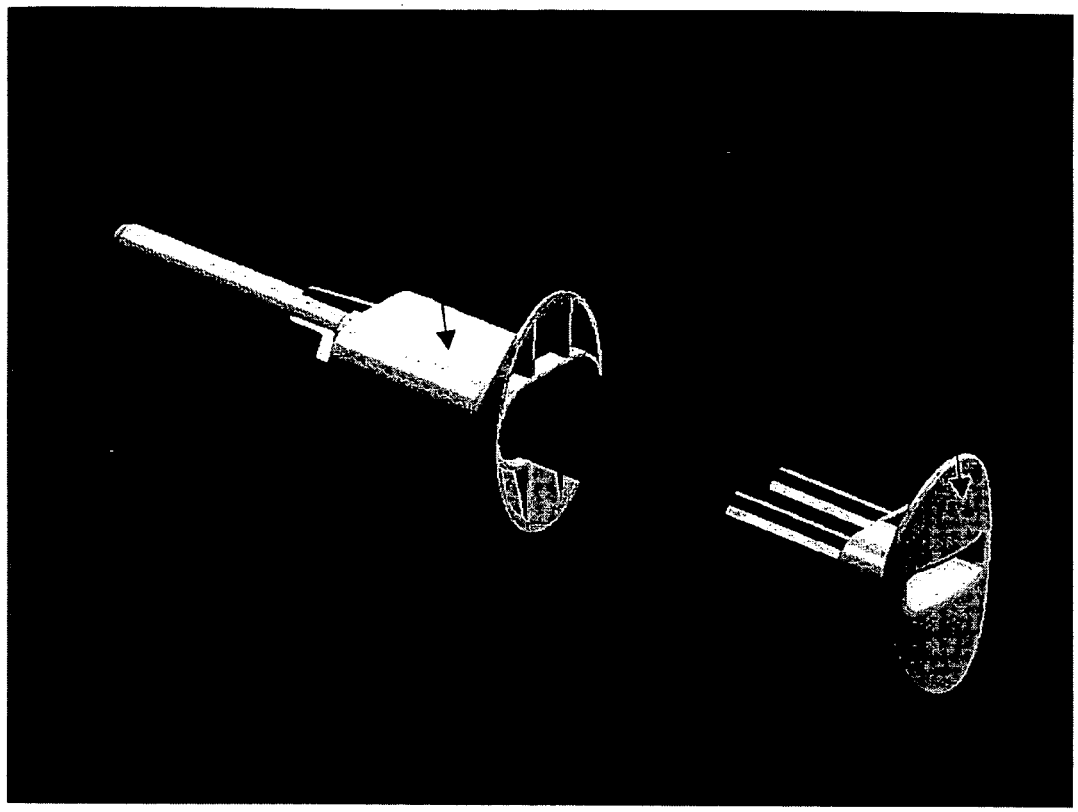
FIG. 30 is a perspective, partially cut away view of a plunger according to the invention.

Preferably, the handpiece dispenser is reusable in order to minimize waste. However, in some situations it may be desirable to have a single use device in order to improve asepsis or convenience. An optional single use device has been conceived which utilizes the same cartridge (FIG. 30). The design may include a mixtip that has been augmented with finger flanges. This "winged mixtip" is used in lieu of the regular mixtip and reusable handpiece dispenser described above. A plunger is needed to activate the pistons. A single-use plunger may be provided that has thinner wall sections to minimize waste (FIG. 27). The single use configuration is sometimes referred to as the disposable system. Even though the reusable handpiece offers ergonomic benefits over the single use system, some users will recognize the benefits of a fully disposable system.

The volume of the cartridge can be specifically tailored to the desired volume by changing the length and/or the bore diameter. In one embodiment, there is one standard base cartridge. Adding extensions onto the base unit makes cartridges that have greater volume and deliver more product (FIGS. 12 and 31). The extensions are formed as a contiguous part of the base unit during molding of the cartridge, which is accomplished by having a mold insert for each desired extension.

While the outer diameter of the cylinders is held constant, the core pins used to form the inner diameter of the cartridge bores can be changed to further modify the volume (FIG. 32-35). The variable bores are maintained on the same axis, so that they can be used with a universal handpiece. One practical configuration allows for three bore diameters; 0.200, 0.225 and 0.250 inches. Conceivably, the inner diameter of this configuration could vary infinitely between 0.200 and 0.250 inches. It should be recognized that this concept is not just limited to these sizes and that other sizes could be configured to achieve similar results.

Figures 36, 37:
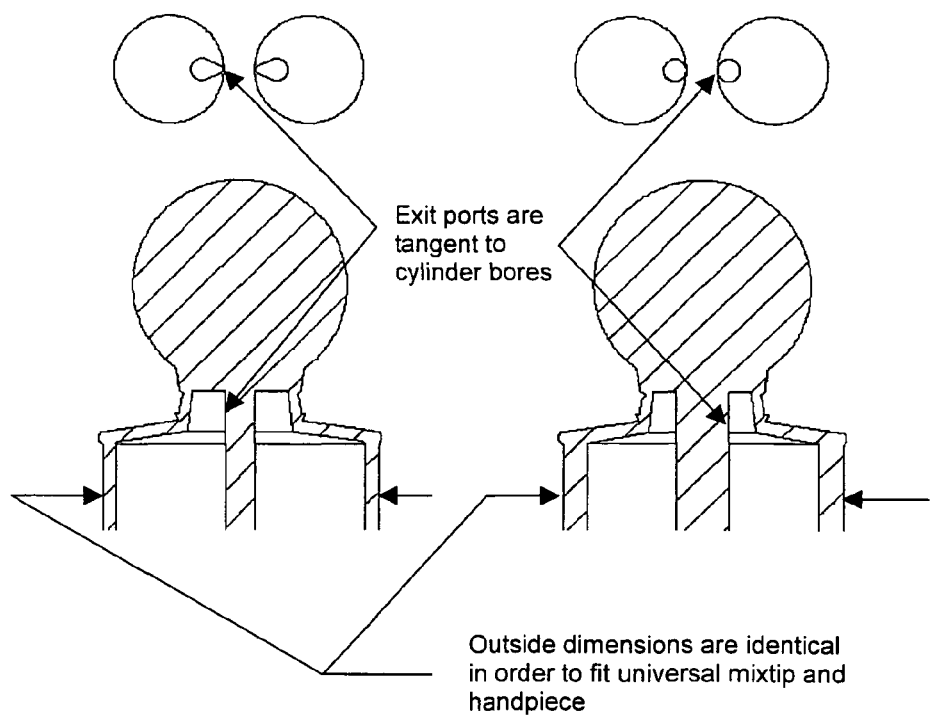
FIG. 36 shows a front sectional view of one portion of one device as in FIG. 31.
FIG. 37 shows a front sectional view of one portion of one device as in FIG. 31.

To further explain the relationship between the bore diameter and the exit ports, it is necessary to understand that the exit ports are placed as close together as possible. This minimizes the length of the breaking ligament, so that it breaks easily. The closest the exit ports can be positioned is the point of tangency of the smallest bore size (FIG. 36-37). In this configuration, it is the 0.200 in. diameter bore size. Keeping the bores and exit ports on the same center to center axis and increasing the bore size permits the size of the exit ports to be increased by extending a lobe to the tangency of the larger bore size. In this configuration, all of the aforementioned changes to the bore diameters and exit ports are done within the outer surface periphery of the base unit cartridge. Consequently, a universal mixtip and handpiece can accommodate many different cartridge variations.

Figure 38:
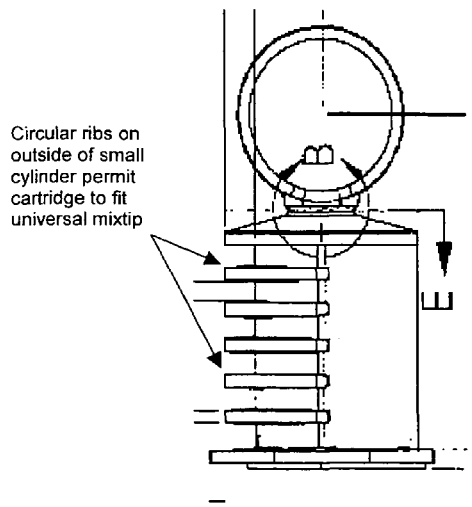
FIG. 38 shows a front elevational view of an alternative device according to the present invention.
Figure 39:
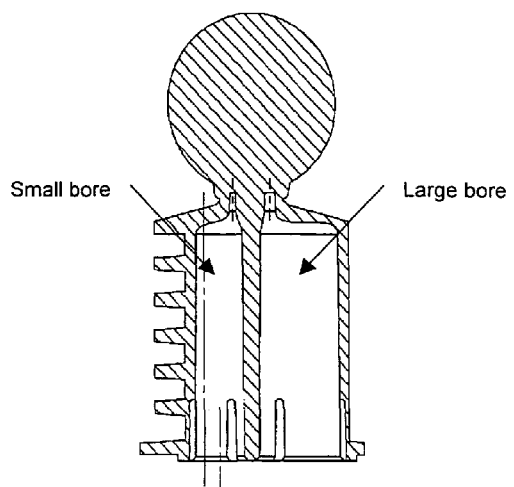
FIG. 39 shows a front sectional view of a device as in FIG. 38.
Figure 40:
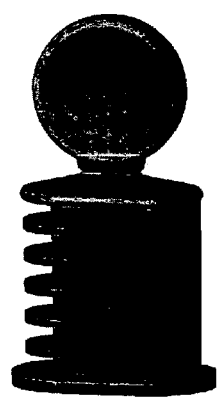
FIG. 40 shows a perspective view of a device as in FIG. 38.

In an embodiment of the invention, the cylinders can be different sizes in order to accommodate products with mix ratios other than 1:1. For example, a product with a 3:1 mix ratio could be delivered by having one small bore and one large bore (FIGS. 38-40). When molding plastic components it is desirable to have uniform wall thickness, so ribs could be utilized to keep the wall thickness consistent. In order to fit a universal mixtip, the ribs would take up the same space as the outer periphery of the base cartridge (FIG. 40).

A finite element analysis study (FEA) determined that the optimal cross section for the breaking ligament is the figure-8 shape as shown in FIGS. 32-35 and 41-48. The FEA determined that this shape in conjunction with the V-groove (FIG. 10) produces stress concentration, which results in a uniform fracture along the intended plane. This holds true for both bending and torsional fracture modes.

The cross section of the inventive cartridge neck is oval but it could even be circular as shown below (FIGS. 41-48). A circular neck would require a similarly shaped circular pocket in the mixtip and would have the added benefit of having a more uniform distribution of forces than the oval configuration. Conceivably, this would result in better sealing characteristics and less backflow.

An intra-oral tip (FIGS. 49-54) is used for those product applications where precise application is needed such as the dual-phase impression technique mentioned earlier. The intra-oral tip snaps into the end of the mixtip and can freely rotate 360°. FIG. 28 illustrates the intra-oral tip assembled to the mixtip.

Various alterations and modifications of the invention will be apparent to those of ordinary skill in the art without departing from the scope and spirit of this invention. Accordingly, it should be understood that the invention is not limited to the illustrative embodiments set forth herein.

What is claimed is:

1. A package for the storage and dispensing of a plurality of materials comprising:
a first and a second longitudinally juxtaposed barrels;
each said barrel having a first and a second end;
each said first and second barrels having a quantity of at least one of the materials initially contained therein;
each said barrel having an open end and a dispensing end;
a sealing plunger disposed in each said barrel such that the material in each said barrel is initially positioned between said dispensing end of said barrels and the respective ones of said sealing plungers;
a snap cap contiguously formed to initially close each of said dispensing ends of said barrels; such that said snap cap may be broken from said barrels to form a secondary open end at said dispensing end of said barrels, thereby facilitating the material contained in each said barrel to flow through and be dispensed;
wherein the dispensing ends and the snap cap form a neck area as a section of reduced thickness which is defined by a V-groove that runs around the perimeter of the neck area in a figure 8 shape, whereby the V-groove acts to concentrate the stress across the neck in such a way that said snap cap may be broken from said barrels along a breaking plane;
wherein said snap cap includes a tab portion opposite the neck area, the tab portion being of a sufficient size to allow a user to apply enough leverage to the tab portion to break said snap cap at the section of reduced thickness.

2. The package of claim 1, further comprising:
a mix-tip removably affixed to said first and second barrels and having a dispensing aperture, such that the material that is dispensed from said secondary openings is caused to flow through said mixtip, and out through said dispensing aperture; and
a static mixing element contained within said mixtip to promote intimate contact and mixing of the materials.

3. A storing and dispensing system of a plurality of materials comprising:
a first and a second longitudinally juxtaposed barrels;
each said barrel having a first and a second end;
each said first and second barrels having a quantity of at least one of the materials initially contained therein;
each said barrel having a primary open end and a dispensing end;
a sealing plunger disposed in each said barrel such that the material in each said barrel is initially positioned between said dispensing end of said barrels and the respective ones of said sealing plungers;
a snap cap contiguously formed to initially close each of said dispensing ends of said barrels; such that said snap cap may be broken from said barrels to form a secondary open end at said dispensing end of said barrels, thereby facilitating the material contained in each said barrel to flow through and be dispensed; and,
a dispensing gun having a first and a seconded laterally displaceable gun plungers, and an actuating means for laterally displacing said gun plungers; said first and second barrels having means to removably affix said barrels to said gun; said first gun plunger being receivable within said primary open end of said first barrel, and being laterally displaceable therethrough to contact said seal plunger located in said first barrel; and, said second gun plunger being receivable within said primary open end of said second barrel, and being laterally displaceable therethrough to contact said seal plunger located in said second barrel;
wherein the dispensing ends and the snap cap form a neck area as a section of reduced thickness which is defined by a V-groove that runs around the perimeter of the neck area in a figure 8 shape, whereby the V-groove acts to concentrate the stress across the neck in such a way that said snap cap may be broken from said barrels along a breaking plane;
wherein said snap cap includes a tab portion opposite the neck area, the tab portion being of a sufficient size to allow a user to apply enough leverage to the tab portion to break said snap cap at the section of reduced thickness.

4. The storing and dispensing system of claim 3, further comprising a foil seal initially closing said primary open ends of said first and second barrels, such that when said gun plungers are caused to be laterally displaced into and received by said barrels, said foil seal is first caused to be punctured by physical contact with said gun plungers.

* * * * *